United States Patent
Slocum et al.

(10) Patent No.: US 10,925,655 B2
(45) Date of Patent: Feb. 23, 2021

(54) BONE REDUCTION FORCEPS

(71) Applicant: Massachusetts Institute of Technology, Cambridge, MA (US)

(72) Inventors: Alexander Henry Slocum, Bow, NH (US); James Francis Connor, Jr., Cambridge, MA (US); Jacob Alexander Mooney, Westford, MA (US); Nicholas Wing-Ping Kwok, Novato, CA (US)

(73) Assignee: Massachusetts Institute of Technology, Cambridge, MA (US)

(*) Notice: Subject to any disclaimer, the term of this patent is extended or adjusted under 35 U.S.C. 154(b) by 306 days.

(21) Appl. No.: 16/312,607

(22) PCT Filed: Jul. 6, 2017

(86) PCT No.: PCT/US2017/040935
§ 371 (c)(1),
(2) Date: Dec. 21, 2018

(87) PCT Pub. No.: WO2018/009691
PCT Pub. Date: Jan. 11, 2018

(65) Prior Publication Data
US 2019/0328434 A1   Oct. 31, 2019

Related U.S. Application Data

(60) Provisional application No. 62/360,094, filed on Jul. 8, 2016.

(51) Int. Cl.
*A61F 2/46* (2006.01)
*A61B 17/88* (2006.01)
(Continued)

(52) U.S. Cl.
CPC ...... *A61B 17/8866* (2013.01); *A61B 17/2812* (2013.01); *A61B 2017/00407* (2013.01); *A61B 2017/2837* (2013.01)

(58) Field of Classification Search
USPC ..... 606/324–328, 151, 157, 51–52, 205–211
See application file for complete search history.

(56) References Cited

U.S. PATENT DOCUMENTS 5,578,032 A    11/1996  Lalonde
8,529,575 B2    9/2013  Tsai et al.
(Continued)

OTHER PUBLICATIONS

International Searching Authority Authorized Officer: Blaine R. Copenheaver, Notification of Transmittal of the International Search Report and the Written Opinion of the International Searching Authority, or the Declaration; PCT/US2017/040935, 17 pages, dated Sep. 13, 2017.

(Continued)

*Primary Examiner* — Sameh R Boles
(74) *Attorney, Agent, or Firm* — Sunstein LLP

(57) ABSTRACT

Bone reduction forceps provide both continuous and discrete adjustment of force. A worm gear rotatably attached to one arm of the forceps engages a rack attached to another arm of the forceps to provide both the continuous and discrete force adjustment. Buttress threads on the worm and/or the rack allow for rapid closure by squeezing the handles of the forceps. Rotating the worm gear allows for fine adjustment of closing force. A five-bar linkage provides increased mechanical advantage and an extra degree of freedom, compared to conventional forceps. Interchangeable tips provide flexibility, allowing a user to customize the forceps to a task or the user's preferences.

23 Claims, 15 Drawing Sheets

(51) Int. Cl.
*A61B 17/28* (2006.01)
*A61B 17/00* (2006.01)

(56) References Cited

U.S. PATENT DOCUMENTS

2011/0256502 A1\* 10/2011 Katz .................. A61C 3/14
                                                    433/114
2012/0271366 A1    10/2012 Katrana et al.

OTHER PUBLICATIONS

Kalinowska, Ola, et al., "Novel Forceps for Reduction of Fractured Metacarpal and Phalangeal Bones," *ASME—2.750 Medical Device Design*, 12 pages, Fall 2015.

\* cited by examiner

BONE REDUCTION FORCEPS

CROSS-REFERENCE TO RELATED APPLICATIONS

This application claims the benefit of U.S. Provisional Patent Application No. 62/360,094, filed Jul. 8, 2016, titled "Bone Reduction Forceps," the entire contents of which are hereby incorporated by reference herein, for all purposes.

TECHNICAL FIELD

The present invention relates to bone reduction forceps and, more particularly, to forceps that provide continuously adjustable clamping force.

BACKGROUND ART

Bone fractures often require surgical intervention to heal properly. "Reduction" is a surgical procedure to restore a fracture or a dislocation to a correct anatomical alignment. In this sense, "reduction" does not refer to removal or a quantitative decrease of anything. Instead, "reduction" refers to restoration, as in "bringing back to normal." Fractured bones lose their normal alignment in the form of lateral and/or longitudinal displacement of bone fragments, relative to each other, and/or angulation (differential rotations about their longitudinal axes). To facilitate proper healing, the bone fragments must be re-aligned to their normal anatomical positions. Orthopedic surgeons recreate the normal alignment of the bone fragments by "reduction" of the displacement and/or angulation.

Reduction of fractures in hands is among the most common procedures in hand orthopedic surgery. The most critical steps in proper fracture reduction are the alignment of the fractured fragments and their temporary fixation. These steps are currently achieved using an industry-standard set of bone reduction forceps, but these forceps pose a number of problems.

Bone reduction forceps are an important instrument used to manipulate bone fragments and hold them in place during surgery. Conventional bone reduction forceps are scissor-like, in that they include two pivoted arms. One end of each arm generally includes a finger- or palm-engaging loop or handle. The other ends of the arms define counterfacing jaws or pointed tips that are used to grasp the bone fragments.

Some conventional bone reduction forceps include counterfacing ratcheting racks to lock the two arms, relative to each other and, thereby, maintain a force between the jaws or tips to hold the bone fragments together after the forceps have been released from a surgeon's hand. Elastic deformation of the arms provides the force. Other conventional bone reduction forceps include leadscrews to maintain a set amount of force.

However, these conventional bone reduction forceps have shortcomings. The amount of force that conventional ratcheting rack forceps can maintain is characterized by discrete increments, where the number of steps equals the number of possibly mechanical engagements between the counterfacing racks, whereby engagement of rack teeth forces a fixed displacement increment that leads to cumulative displacement x, which given the elasticity (spring rate k) of the clamp, creates a force in accordance with the relation $F=k\,x$. Typical conventional bone reduction forceps provide about eight steps (levels) of force, where each level is about 10 N greater than the previous step. Often, surgeons find that one step provides insufficient force, but the next step provides too much force. Furthermore, once locked together, the amount of force cannot be reduced, without completely disengaging the racks from each other, which then effectively requires the surgeon to start over, thereby increasing the time required to complete the operation.

Forceps with leadscrews are disfavored by surgeons for ergonomic reasons. Because the screw is a positive engagement mechanism, the screw (or a nut) must be turned to close or open the forceps, and thus the forceps cannot be quickly closed or opened (disengaged) if needed. In addition, internal thread features in the nut can be difficult to sterilize. Furthermore, these leadscrews have left handed threads, making them awkward and unnatural to use.

SUMMARY OF EMBODIMENTS

An embodiment of the present invention provides bone reduction forceps. The bone reduction forceps include a first arm and a second arm. The first arm has a handle proximate one end and a first bone-engaging tip proximate an opposite end. The second arm has a handle proximate one end and a second bone-engaging tip proximate an opposite end. The second arm is pivotally attached to the first arm by a first joint. The first joint is disposed between the respective handles and the respective bone-engaging tips of the first and second arms. A rack is attached to the first arm, between the first joint and the handle of the first arm. A worm gear is rotatably attached to the second arm, between the first joint and the handle of the second arm. The worm gear is oriented and configured to engage the rack.

The rack may include a curved planar rack attached to the first arm, between the first joint and the handle of the first arm. The rack may extend (arc) toward the second arm and pass beneath the second arm, wherein a center of the radius of the rack is disposed at the first joint.

The bone reduction forceps may also include a thumbwheel attached for rotation with the worm gear. The thumbwheel may be an integral part of the worm gear.

The rack and the worm gear may collectively form a ratchet action, in which at least one tooth (flight) of the worm gear engages the rack, and elastic deformation of the rack allows the teeth of the worm gear to skip over the teeth of the rack, such as for rapid closing of the forceps.

The rack may include a plurality of teeth. Each tooth may have a respective slip side face and a respective lock side face. The slip side face may form an angle of about 25-65°, relative to a normal axis between the rack and the worm gear. The lock side face may form an angle of about 0-20°, relative to the normal axis. The rack may be arc-shaped, with the center of the arc at the center of the pivot joint that connects the handles so, as the rack moves relative to the worm gear and the handles open or close, tooth contact is maintained.

In another embodiment, the slip side face may form an angle of about 25-65°, relative to a normal axis between the rack and the worm gear, and the lock side face may form an angle of about 0-20°, relative to a line perpendicular to a rotation axis of the worm gear.

The rack may include a plurality of teeth having a pitch of about 1/18 inch (1.4 mm).

At least one of the bone-engaging tips, i.e., at lease one tip of the first bone-engaging tip and the second bone-engaging tip, may define a curved surface. In at least one mode, the curved surface may counterface the other tip.

The bone reduction forceps may include a five-bar linkage. Each of the first and second arms may include a first portion and a second portion. The first portion may include the handle of the respective arm and a portion of the first joint. The second portion may include the bone-engaging tip of the respective arm. An end of the first portion, opposite the handle, may be pivotally attached to an end of the second portion, opposite the bone-engaging tip, by a respective second joint. One end of a connecting link may be pivotally attached to the second portion of the first arm, between the bone-engaging tip of the first arm and the end opposite the bone-engaging tip of the first arm, by a third joint. Another end of the connecting link may be pivotally attached to the second portion of the second arm, between the bone-engaging tip of the second arm and the end opposite the bone-engaging tip of the second arm, by a fourth joint. The first and second portions of the first arm, the first and second portions of the second arm, the connecting link and the first, second, third and fourth joints thus may collectively form the five-bar linkage.

The first bone-engaging tip may be reattachably attached to the first arm, and the second bone-engaging tip may be reattachably attached to the second arm. Each bone-engaging tip may be reattachably attached to the respective arm by a respective threaded connector, or by a respective Luer lock connector, or by a respective press fit connector or by a respective self-locking taper fit connector.

The bone-engaging tip of the first arm may include a one-prong tip, and the bone-engaging tip of the second arm may include a one-prong tip. The bone reduction forceps may further include a third bone-engaging tip that has a two-prong tip. The third bone-engaging tip may be reattachably attachable to the first arm in place of the one-prong bone-engaging tip of the first arm.

Another embodiment of the present invention provides bone reduction forceps that include a five-bar linkage. The bone reduction forceps include a first arm and a second arm. The first arm has a handle proximate one end and a bone-engaging tip proximate an opposite end of the first arm. The second arm has a handle proximate one end and a bone-engaging tip proximate an opposite end of the second arm. The second arm is pivotally attached to the first arm by a first joint. The first joint is disposed between the respective handles and the respective bone-engaging tips of the first and second arms. A rack is attached to the first arm, between the first joint and the handle of the first arm. At least one tooth is attached to the second arm. The at least one tooth is configured to engage the rack.

Each of the first and second arms includes a first portion and a second portion. The first portion includes the handle of the respective arm and a portion of the first joint. The second portion includes the bone-engaging tip of the respective arm. An end of the first portion, opposite the handle, is pivotally attached to an end of the second portion, opposite the bone-engaging tip, by a respective second joint. One end of a connecting link is pivotally attached to the second portion of the first arm, between the bone-engaging tip of the first arm and the end opposite the bone-engaging tip of the first arm, by a third joint. Another end of the connecting link is pivotally attached to the second portion of the second arm, between the bone-engaging tip of the second arm and the end opposite the bone-engaging tip of the second arm, by a fourth joint. The first and second portions of the first arm, the first and second portions of the second arm, the connecting link and the first, second, third and fourth joints thus collectively form the five-bar linkage.

Yet another embodiment of the present invention provides bone reduction forceps that have reattachable tips. The bone reduction forceps include a first arm and a second arm. The first arm has a handle proximate one end and a first reattachably attached bone-engaging tip proximate an opposite end of the first arm. The second arm has a handle proximate one end and a second reattachably attached bone-engaging tip proximate an opposite end of the second arm. The second arm is pivotally attached to the first arm by a first joint disposed between the respective handles and the respective bone-engaging tips of the first and second arms. A rack is attached to the first arm, between the first joint and the handle of the first arm.

Each bone-engaging tip may be reattachably attached to the respective arm by a respective threaded connector, or by a respective Luer lock connector, or by a respective press fit connector or by a respective self-locking taper fit connector.

BRIEF DESCRIPTION OF THE SEVERAL VIEWS OF THE DRAWING

The invention will be more fully understood by referring to the following Detailed Description of Specific Embodiments in conjunction with the Drawings, of which.

DETAILED DESCRIPTION OF SPECIFIC EMBODIMENTS

Bone reduction forceps disclosed herein are comfortable and easy to use, yet they are more effective than conventional forceps in achieving desired clamping force and necessary stability. The forceps clamp bone fragments with a finely adjustable force, they can be loosened in a controlled manner without losing alignment and they provide more grip stability upon fixation, thereby making it easier and faster to achieve anatomic alignment in fracture reduction, leading to decreased surgical time and increased user satisfaction.

The forceps enable both continuous and rapid discrete adjustment of force with the ability to instantly disengage. A worm gear with a buttress thread form rotatably attached to one arm of the forceps engages a rack attached to another arm of the forceps to provide both the continuous and discrete force adjustment, where turning the worm gear displaces the rack to control the forceps closure with fine resolution or pushing down on the rack disengages it from the worm gear allowing for instant opening of the forceps, or squeezing the forceps closed allows the worm gear teeth to skip on the rack teeth for rapid closure.

A five-bar linkage provides increased mechanical advantage and an extra degree of freedom, compared to conventional forceps. Interchangeable tips provide flexibility, allowing a user to customize the forceps to a task or the user's preferences. Forceps, according to various embodiments of the present invention, may include one or more of the worm gear, the five-bar linkage and/or the interchangeable tips, in any combination.

As used herein, with reference to embodiments of the present invention and in the claims, the term "tip" or "bone-engaging tip" means a portion of forceps that contacts bone, in the course of using the forceps in an ordinary manner, as described herein. One or more of the tips may be pointed, blunt, flat, concave or have another shape. One or more of the tips may be serrated, roughened or be otherwise patterned to increase contact pressure per unit area, thereby improving grip. The bone need not necessarily be contacted by an apex of the tip. The bone may, for example, be contacted by a side or face of the tip acting as a jaw. The definition of the term "tip" includes "jaw."

Conventional Forceps

Figure 1:
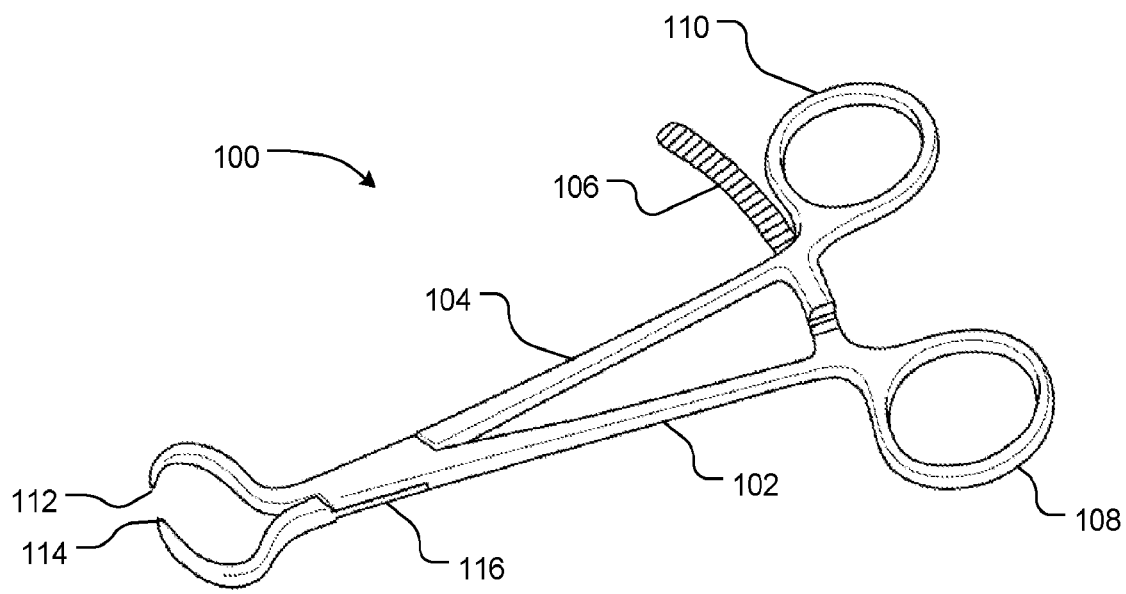
FIG. 1 is a perspective view of bone reduction forceps, according to the prior art.
Figure 2:
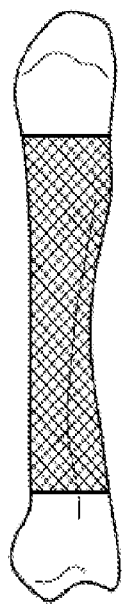
FIGS. 2-5 schematically illustrate examples of unfractured bone and transverse, oblique and comminuted fractures, respectively, as known in the prior art.
Figure 3:
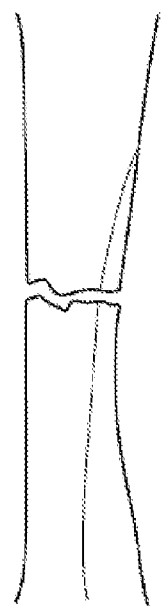
Figure 4:
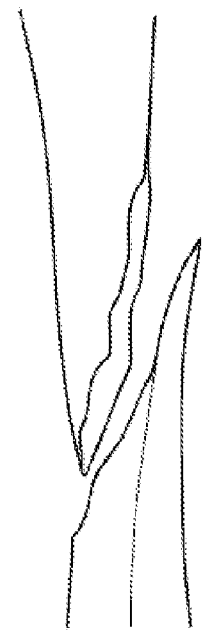
Figure 5:
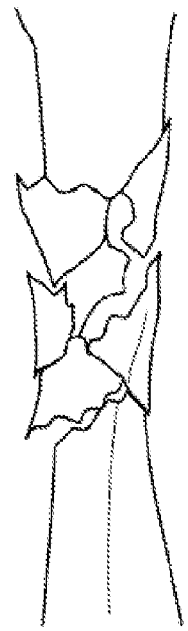

FIG. 1 is a perspective view of one type of bone reduction forceps 100, according to the prior art. The prior art forceps 100 include two arms 102 and 104 and a curved rack 106 attached to one of the arms 104. The arms 102 and 104 have handles 108 and 110 proximate respective ends of the arms 102 and 104. The arms 102 and 104 also have bone-engaging tips 112 and 114 proximate opposite respective ends of the arms 102 and 104. The arms 102 and 104 are pivotally attached to each other by a single joint 116. The rack 106 acts as a "ratcheting" mechanism, providing quick setting, quick release and several discrete force levels. Conventional ratcheted forceps 100 have utility, because they allow for fast, gross (discrete increments) adjustment of the forceps, a crucial feature in surgery, in which time is critical. However, without fine control, they often are either too tight or too loose, thus sometimes making it difficult to achieve fine anatomic alignment of bone fragments, which is often required in hand surgery for example.

Figure 6:
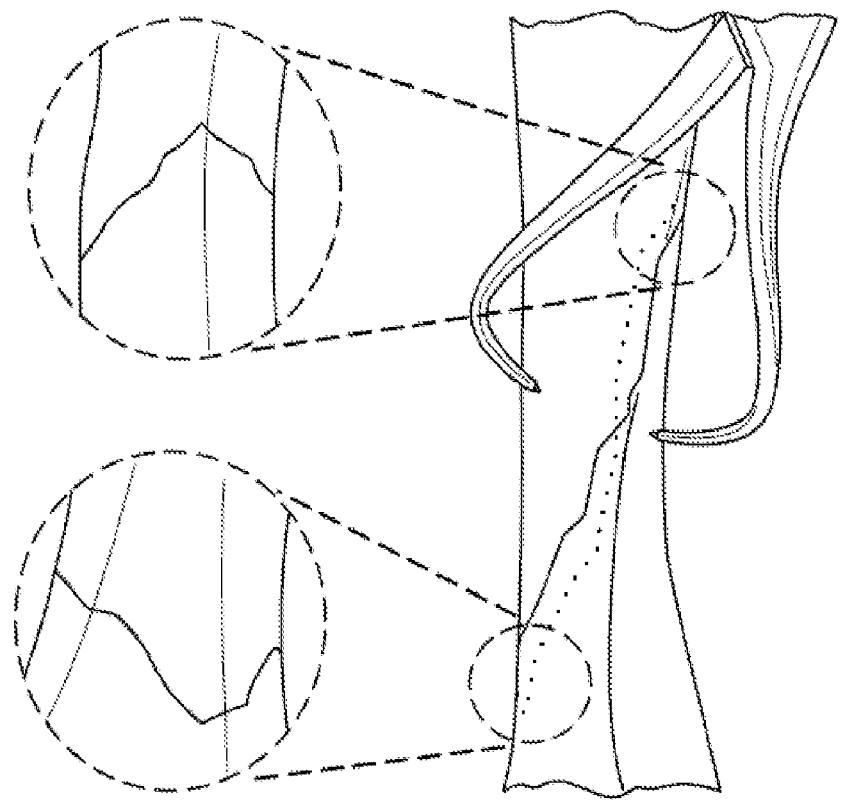
FIG. 6 schematically illustrates an example of an oblique fracture reduced to anatomic alignment with conventional bone reduction forceps, as practiced in the prior art.

There are approximately 182,471 hand fractures treated in the United States each year involving the metacarpals and phalangeal bones [1]. Metacarpal and phalangeal fractures are generally treated operatively if the deformity may interfere with normal function [2]. There are three types of fractures: transverse, oblique, and comminuted. Transverse fractures occur when the fracture is perpendicular to the long axis of the bone, oblique when the fracture is slanted across the long axis of the bone, and comminuted when multiple fragments are present, as illustrated in FIGS. 2-5 [3]. During operative treatment, oblique fractures are reduced to anatomic alignment using a single bone reduction forceps, as illustrated in FIG. 6, while transverse fractures sometimes require two forceps to achieve alignment.

Hand fractures often require surgical intervention to heal properly [4]. Bone reduction forceps are one of the most important instruments used in bone reduction surgery. In such surgery, a surgeon uses forceps to manipulate bone fragments. This surgical intervention includes six steps [5]. First, the (1) fracture is dissected and (2) traction is applied to move the bone fragments close together. The bone reduction forceps are then used to (3) bring the bone fragments into surgical alignment and (4) temporarily fixate them together. An (5) intraoperative x-ray is conducted to ensure proper alignment was achieved, and if so, (6) bones are permanently fixated together via additional hardware. Steps three and four are considered the most challenging and critical portions of the operation, often requiring multiple iterations before the bone fragments are securely held in surgical alignment. The difficulty associated with these steps is attributed to design limitations of conventional bone reduction forceps.

Conventional ratcheting bone reduction forceps 100 can be tightened in only discrete steps, and they cannot be partially loosened. To reduce the clamping force, the forceps 100 must be first fully released, then increased to the desired force, making it difficult for a surgeon to apply the correct amount of force to securely fixate the bone fragments together; typically, either the fragments are held too loosely or too tightly. In the former scenario, the bones risk becoming misaligned during the imaging or permanent fixation stages, while in the latter, the higher force pushes the bones out of alignment [5]. In both scenarios, the surgeon is forced to restart at step three in the surgery. Thus, although simple to use, the ratcheting rack 106 allows neither continuous (as opposed to discrete) adjustment of force, nor partial reduction of force.

In addition, although the pointed tips 112 and 114 can effectively achieve anatomic alignment and stable clamping, they constrain only five degrees of freedom. Consequently, during surgery, the forceps 100 may rotate and collide with nearby objects, prematurely releasing. Some forceps (not shown) have serrated jaws. However, such forceps can be applied only perpendicular to the long axis of the bone, and thus are less commonly used.

Furthermore, the tip geometry of the forceps 100 poses issues. The tips 112 and 114 have a range of motion much larger than bone diameters. Consequently, the tips 112 and 114 often catch on soft tissue surrounding the surgical site and sometimes offer a suboptimal number of point contacts on the bone [5]. All of these issues contribute to increased surgical time and increased risk of not achieving anatomic alignment.

Another type of conventional forceps (not shown) uses a leadscrew, rather than the rack 106. Leadscrews in forceps generally have left handed threads, making their operation counter-intuitive, thus they are disliked by many surgeons. Although this type of forceps enables fine adjustment of force applied to bone, it is slow and cumbersome to use, because it does not allow for rapid closure or release, and it often does not allow for a complete release, which many surgeons would find useful.

All known bone reduction forceps use first class lever mechanisms to provide mechanical advantage. A first class lever has, as a fulcrum, a pivot joint connected to the lever arm. Effort is applied to the lever arm on one side of the fulcrum, and resistance or load is applied on the other side. Examples of first class levers include seesaws, crowbars and scissors. Mechanical advantage may be greater than, less than, or equal to 1.

No known device overcomes all of the above limitations. Specifically, no known forceps provide stability during collisions, continuous increase and decrease of force, complete release and low risk of soft tissue damage.

Embodiments of the present invention overcome limitations of current forceps. Forceps disclosed herein allow for both discrete and continuous force application to clamp bone fragments together via a worm gear and rack mechanism. Additionally, a 5-bar linkage provides an additional degree of freedom at the tips to better secure the bone fragments, and replaceable tips, on either a first class mechanism or on a five bar mechanism, enable a surgeon to easily customize the forceps for the particular surgical situation.

Functional Requirements

Various embodiments of the present invention meet one or more of several functional requirements to facilitate obtaining and maintaining anatomic alignment of fractured bone. Forceps should be capable of clamping on to hand bones (diameter of about 5 to 15 mm). Forceps should facilitate applying a desired clamping force (about 130 to 150 N). Forceps should reduce risk of damaging surrounding soft tissue, below that posed by conventional forceps. Forceps should be at least as easy and comfortable to use as a conventional devices.

Bone reduction forceps should have physical characteristics that facilitate their use. For example, some embodiments are no longer than about 150 mm and no wider than about 125 mm at the handle when fully opened. Additionally, the handle grip, mechanical advantage and weight are similar to prior art forceps to facilitate adoption by surgeons. Some embodiments amplify a user's force between about 2-3 times and weigh about 70 to 150 g.

Modular Design

Several modular aspects of bone reduction forceps are disclosed to accommodate variability in surgeon preference and to allow for quick adoption in clinical settings. These aspects include: a worm gear and rack locking mechanism, a five-bar linkage and interchangeable tips. These and other aspects are described herein.

Worm Gear and Rack Locking Mechanism

A worm gear and rack provide a continuously-variable locking mechanism, which permits loosening the forceps, as opposed to requiring complete disengagement, as in the prior art. The worm gear, a cylindrical threaded member attached to one handle, engages with a rack attached to the other handle, thereby allowing for relative movement and fixed positioning of the forceps handles. The worm gear is mounted on the one handle to exert a preload force between the thread on the worm gear and the rack teeth, which maintains engagement of the worm gear to the rack. The worm gear and rack locking mechanism may be permanently attached to forceps, or the worm gear may be attached (retrofitted) to existing conventional forceps.

The worm gear thread form preferably is a buttress thread form. As used herein, buttress thread form refers to an asymmetric thread profile often used on leadscrews, not a hydraulic sealing thread form. The thread profile is asymmetric, in that one flank is much steeper than the other flank. For example, one flank may be vertical or near vertical (within about 20° of vertical, i.e., in a range of about 0° to about 20°), and the other flank may have an angle of about 45°±20°, i.e., in a range of about 25° to about 65°. The buttress thread form is designed to handle extremely high axial thrust in one direction. Consequently, a self-locking taper effect in one direction is produced when the worm gear engages the rack.

The rack preferably has a corresponding mating thread form. The steep flanks are engaged such that forces on the forceps' tips that would act to open the forceps, e.g., reaction forces from a bone being gripped, force contact between the steep flank threads of the rack and worm gear and the forceps remain closed. On the other hand, if the surgeon wants to rapidly close the forceps to make initial contact with the bone, forces applied to the handles of the forceps disengage the steep flank threads and engage the inclined flank threads. The resultant tooth separation forces created by the inclines deflect the rack downward and allow the teeth to skip over each other.

Alternatively, the worm or the rack can have a symmetrical thread form, and the other can have an asymmetrical thread form, but this configuration is more prone to accidental skipping if the closure force is high. This is the mechanism by which conventional forceps work, except there is no worm gear, just a single buttress tooth on one handle that engages the rack on the other handle. Replacement of the single tooth with the buttress thread worm gear facilitates embodiments of the present invention to meet the long felt need of surgeons to have forceps with continuously adjustable force and ability to adjust the force up or down with very fine resolution, without having to disengage and re-engage the forceps.

Figure 7:
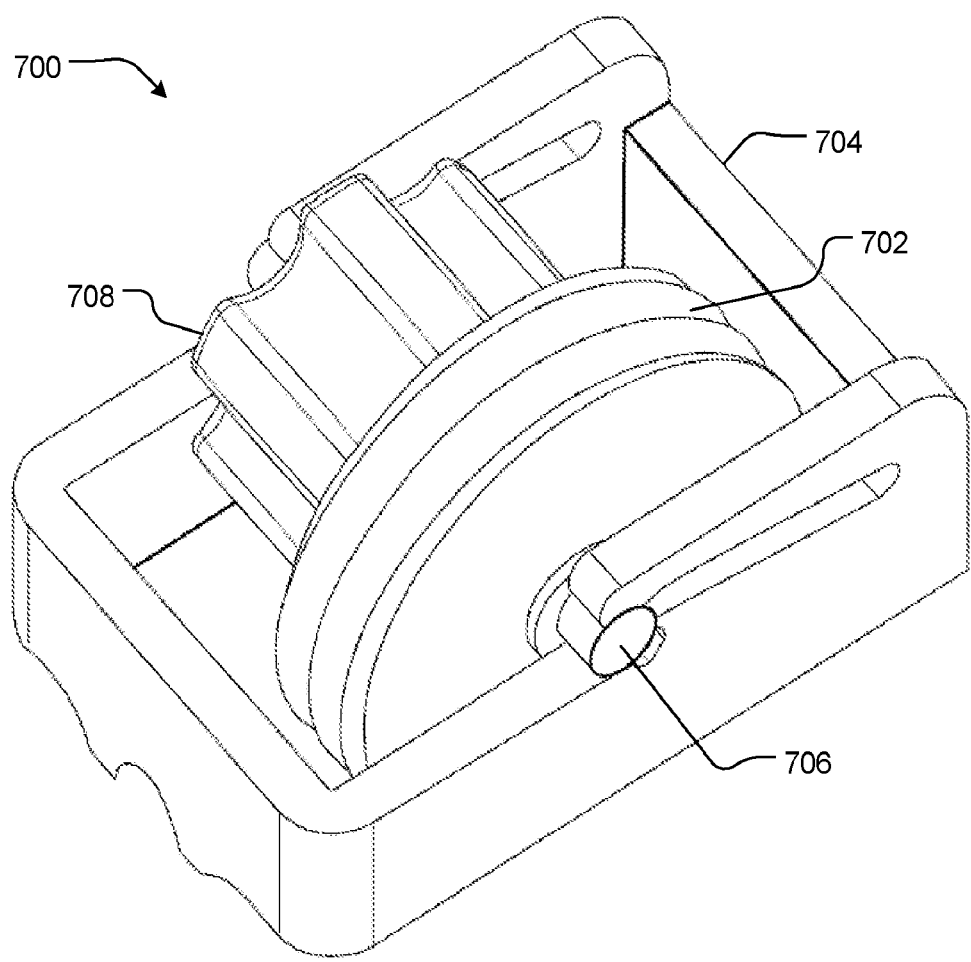
FIG. 7 is a perspective schematic illustration of a worm gear drive for bone reduction forceps, according to an embodiment of the present invention.

FIG. 7 is a perspective schematic illustration of a worm gear drive 700 that is attachable to conventional forceps, such as the forceps 100 shown in FIG. 1. The worm gear drive 700 includes a worm gear 702 rotatably mounted within a rectangular frame 704 by an axle 706. The worm gear drive 700 optionally includes a thumbwheel 708 attached to the worm gear 702 and the axle 706 for rotation therewith. The thumbwheel 708 may be replaced by a knurled cylinder, wheel or other easy-to-engage surface (not shown). Alternatively, the worm gear 702 may be driven with a finger or thumb in direct contact with edges of the flights of the worm gear, which may be knurled or otherwise have features to aid with engagement with the surgeon's finger.

Figure 8:
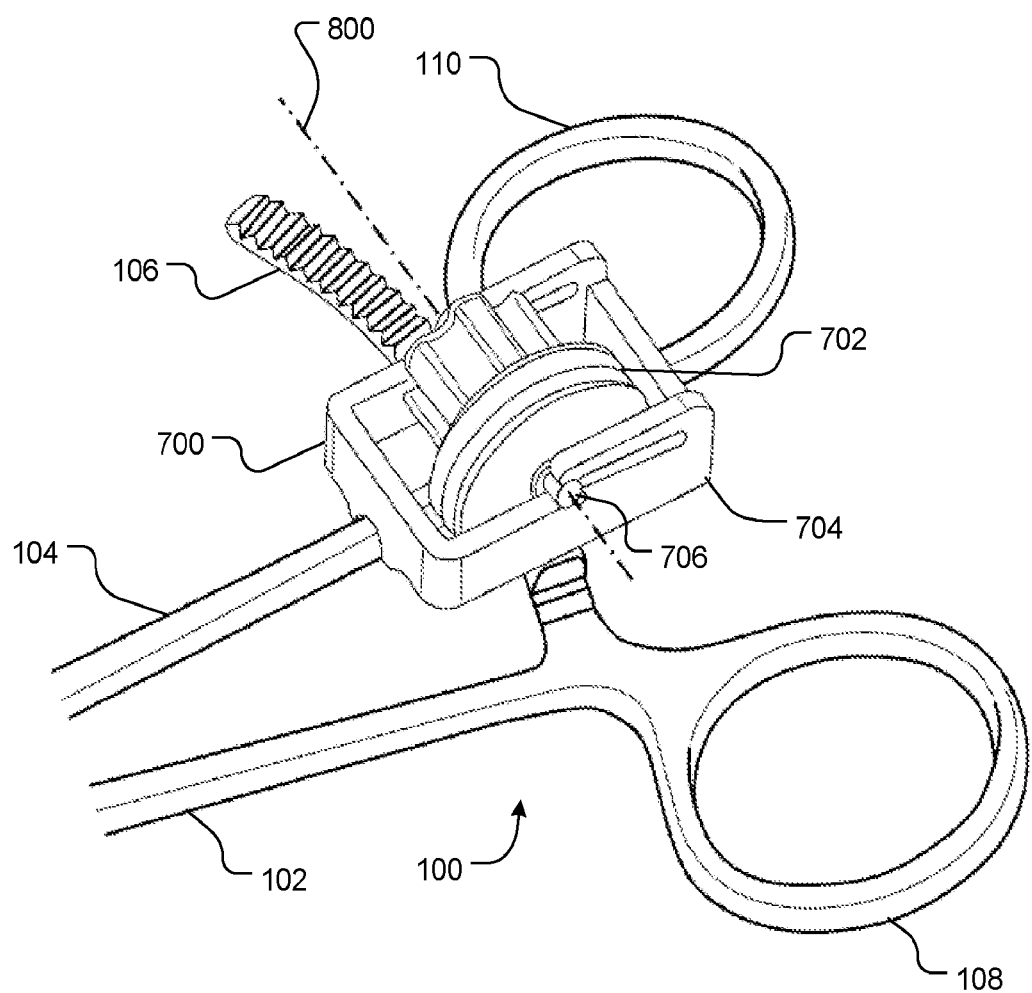
FIG. 8 is a close-up perspective view of the worm gear drive of FIG. 7 attached to the conventional bone reduction forceps of FIG. 1, according to an embodiment of the present invention.

As shown in FIG. 8, the rectangular frame 704 may be integrally formed with, or it may be attached to, the conventional forceps 100, such as by welding or with an adhesive or using a mechanical spring-mounted or screw-mounted bracket (not shown) that clamps onto a portion of the forceps 100, such as onto the arm 104. The latter would be particularly useful for retrofitting some types of existing forceps. The rectangular housing 704 is attached to the conventional forceps, such that the worm gear 702 engages the rack 106 of the forceps 100, forming a rack-and-worm gear combination. Rotating the worm gear 702 therefore opens or closes the arms 102 and 104 of the forceps 100, or at least adjusts force applied by the forceps 100.

The thumbwheel 708 or flights of the worm gear 702 provides a mechanical user interface to the worm gear drive 700, facilitating rotation of the worm gear 702 by a user's thumb or finger (not shown). Thus, conventional forceps 100 may be retrofitted with the worm gear drive 700 of FIG. 7 to gain benefits of other embodiments described herein, such as fine adjustability of forceps tips. The worm gear/thumbwheel/axle 702-708 and the rectangular frame 704 may be made of suitable materials, such as 17-4 precipitation hardened (PH) stainless steel, or other materials acceptable for surgical instruments, as described herein or as known to those skilled in the art.

To rapidly close the forceps, the handles 108 and 110 may be squeezed toward each other and the teeth (flights) of the worm gear 702 skip over the inclined teeth of the rack 106 by causing the rack to bend downwards (a combination of bending deflection of the rack and bending and torsion of the handles). Thus, at least one tooth (flight) of the worm gear 702 can be considered to act like the pawl of a ratchet, but unlike the pawl of a ratchet, the worm gear does not pivot to allow motion of the rack in one direction. Instead, the rack bends down to enable the contacting teeth to skip over each other for rapid closing of the forceps. To rapidly open the forceps, the handles 108 and 110 may be displaced out of plane to pry apart the worm gear 702 and rack teeth 106, and thus allow for free movement of the handles. As used herein, "ratchet" means a mechanism of the worm gear engaging the rack teeth to allow for free motion in the closing direction of the forceps and constrained motion in the opening direction of the forceps.

Similar to the conventional forceps, the rack's buttress thread profile allows ratcheting in only the forward (closing) direction, allowing a surgeon to tighten the forceps without risk of them prematurely unlocking. Relieving the preload force of the rack 106 disengages the worm gear 702 from the rack 106, fully releasing the locking mechanism. However, advantageously, rotating the worm gear 702 allows for fine control over the tightening and loosening of the forceps. Thus, using the worm gear 702 allows the forceps to be loosened without having to be fully disengaged, and the worm gear 702 allows the forceps to be selectively tightened to provide a desired clamping force.

Figure 9:
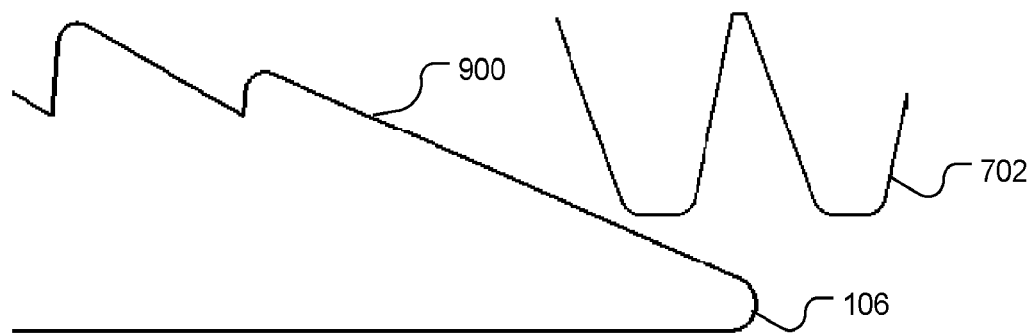
FIG. 9 is a schematic close-up illustration of teeth (flights), in an open position, of the worm gear drive and rack of the bone reduction forceps of FIGS. 7 and 8, according to an embodiment of the present invention.
Figure 10:
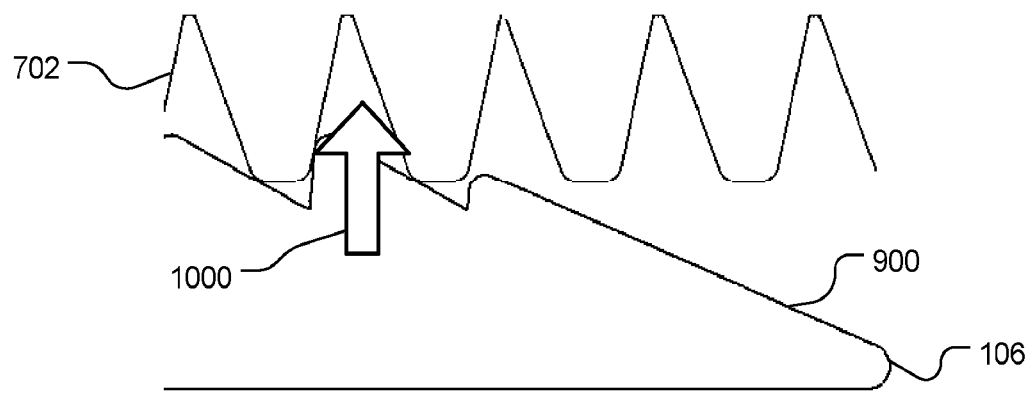
FIG. 10 is a schematic close-up illustration of the teeth of FIG. 9 in a closed position, according to an embodiment of the present invention.
Figure 11:
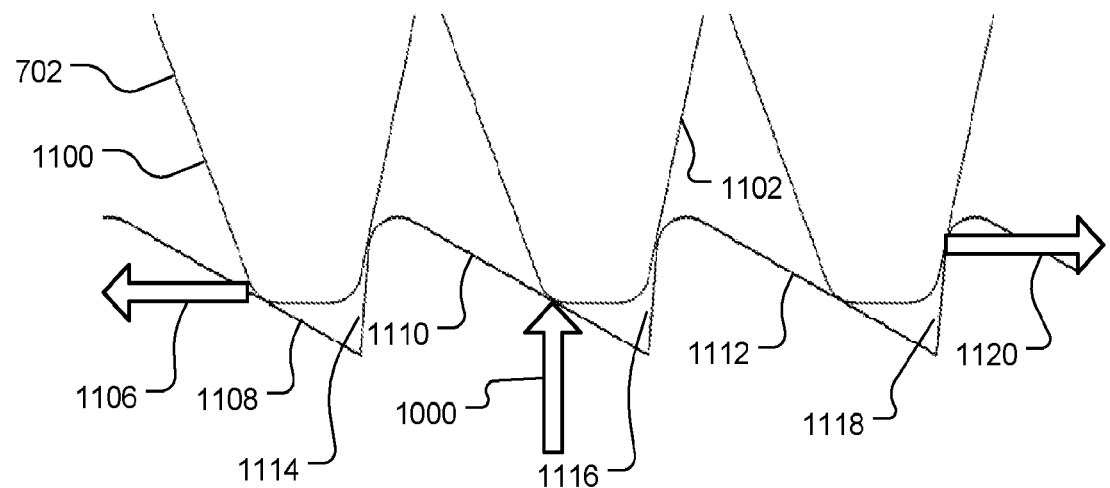
FIG. 11 is another schematic close-up illustration of the teeth of FIG. 9 in the closed position to show forces exerted by and on the teeth, according to an embodiment of the present invention.

The worm gear 702 and rack 106 system operate in two modes: acting as a ratchet and acting as a worm drive. In the mode of operation that provides gross adjustment, the worm gear 702 and rack 106 system operate like a ratchet, similar to conventional reduction forceps. As shown schematically in FIG. 9, the worm gear 702 and the rack 106 are assembled such that the top plane 900 of the rack 106 meets the worm gear 702. When the user closes the device, the worm gear 702 is pressed against the rack 106, and the rack 106 is deflected downwards. This downward deflection creates a resultant normal force ("deflection force"), as indicated by an arrow 1000 in FIG. 10. In this way, the rack 106 inherently acts as a spring in the ratcheting system, with the handles also elastically deforming somewhat to add to the spring action. As shown schematically in FIG. 11, as the user continues to close the device, flights (exemplified by flights 1100, 1102 and 1104) of the worm gear 702 now apply force 1106 against one side (a "slip side," exemplified by slip sides 1108, 1110 and 1112) of each tooth in the rack 106.

For embodiments of the worm gear drive 700 (FIG. 7) that are to be attached to existing conventional forceps, the thread pitch of the worm gear 702 should match the pitch of the rack 106. However, for embodiments that include both the worm gear 702 and the rack, the thread pitches may be the same as, or different from, pitches of conventional forceps. In addition, for embodiments that include a rack, the shape of the teeth of the rack may be different from conventional forceps, as discussed herein.

Figure 12:
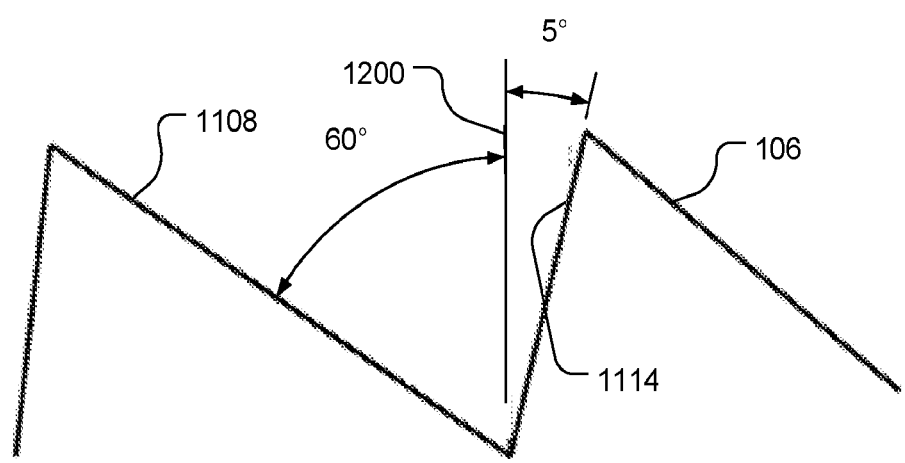
FIG. 12 is a schematic more enlarged illustration of the teeth of FIG. 9 showing tooth face angles, according to an embodiment of the present invention.

For a specific embodiment that includes the rack, as shown in FIG. 12, a rack 106 has a tooth angle chosen such that a significant downward force 1000 is created when the worm tooth engages the inclined flank 1110 of the rack 106. The downward force 1000 increases as the rack 106 moves to the left in response to a force 1106 applied by the surgeon to close the forceps and this causes the rack 106 to deflect downwards until the worm gear 702 is able to move past that rack's tooth and settle into the next position. Conversely, when the user attempts to open the device, the worm gear 702 applies a force against the opposing tooth face (a "lock side," exemplified by lock sides 1114, 1116 and 1118). In this embodiment, the rack 106 has an asymmetric tooth design, in which the tooth angle of the slip side 1108-1112 is relatively large, about 45°±20° (relative to a normal axis 1200 between the rack 106 and the worm gear 702, or relative to a line perpendicular to a rotation axis 800 (FIG. 8) of the worm gear 702, here in this specific embodiment shown as 60°), while the tooth angle of the lock side 1114-1118 is ideally vertical but can be up to 20° and here is shown as 5° to aid in manufacture. The steep angle forms a self-locking taper effect when this side of the tooth is engaged so the rack cannot deflect downward. Thus, when the device is in the lock position, even a large clamping force 1120 cannot generate a deflection force 1000 high enough to cause the rack 106 to deflect to the point where the teeth skip which would undesirably cause the clamping force to be lost. In some embodiments, both the worm gear 702 and the rack 106 have a buttress thread form with near-vertical angles of about 5°.

Exemplary conventional reduction forceps have a rack 106 pitch of approximately 1.4 mm. To maintain a similar ratcheting tactile aspect as what is commonly found in existing devices, some embodiments have a 1/18 inch (1.411 mm) pitch length, as 18 threads per inch (TPI) is a common thread profile and quite similar to 1.4 mm. This pitch length then dictates the angles of the rack 106. To withstand the largest forces possible, the lock side angle should be relatively small to create a self-locking effect where the resulting contact forces acting with the coefficient of friction between the teeth prevent the teeth from sliding past each other. As noted, in one embodiment shown herein, the lock side angle is about 5°, although other small angles between about 0° and about 20° may be used. The larger the inclined flank angle (with respect to vertical) the easier (less force) to rapidly close the forceps, but the larger the pitch and hence the less resolution of control the surgeon will have. Sixty degrees is a good compromise, although for fine motions 45° works well. The limit would be where the self-locking effect ceases, which is a function of the coefficient of friction between the threads, and hence the range of 25°-65° for the inclined thread.

In the fine adjustment clamping mode of operation of the worm gear 702 and rack 106 system, the system operates as a worm drive mechanism to provide fine adjustment of the clamping force $F_{tip}$. With the pitch P of the rack assumed to be that of existing clamps, the diameter D of the worm gear 702 may be chosen to be comfortable for the surgeon to exert a tangential force $T_{applied}$ on the worm gear or thumbwheel surface. Ergonomically, the force should be about 1-10 N. Assuming a sliding efficiency η of the worm gear and a lever ratio α (mechanical advantage of the rack over the tips), the minimum diameter of the worm required is given by Equation 1. Exemplary values are listed in Table 1.

$$D = \frac{F_{tip} P}{\alpha \eta \pi T_{applied}} \quad (1)$$

TABLE 1

Exemplary Values in Calculating Worm Gear Diameter

| | |
|---|---|
| Desired clamp force $F_{tip}$ | 100 N |
| Tangential force from finger, $T_{applied}$ | 4 N |
| Efficiency η | 0.3 |
| Mechanical advantage α | 3 |
| Rack tooth pitch, P | 1.4 mm |
| Minimum diameter of worm, D | 12.4 mm |

In a typical embodiment such as shown herein, a minimum worm gear 702 diameter is about 13 mm, although other diameters may be used in other embodiments. For ease of manufacturing and access purposes, a standard ⅝-18 thread profile may be used, since ⅝ inch (15.875 mm) is larger than the calculated minimum worm gear 702 diameter.

Five-Bar Linkage

Figure 13:
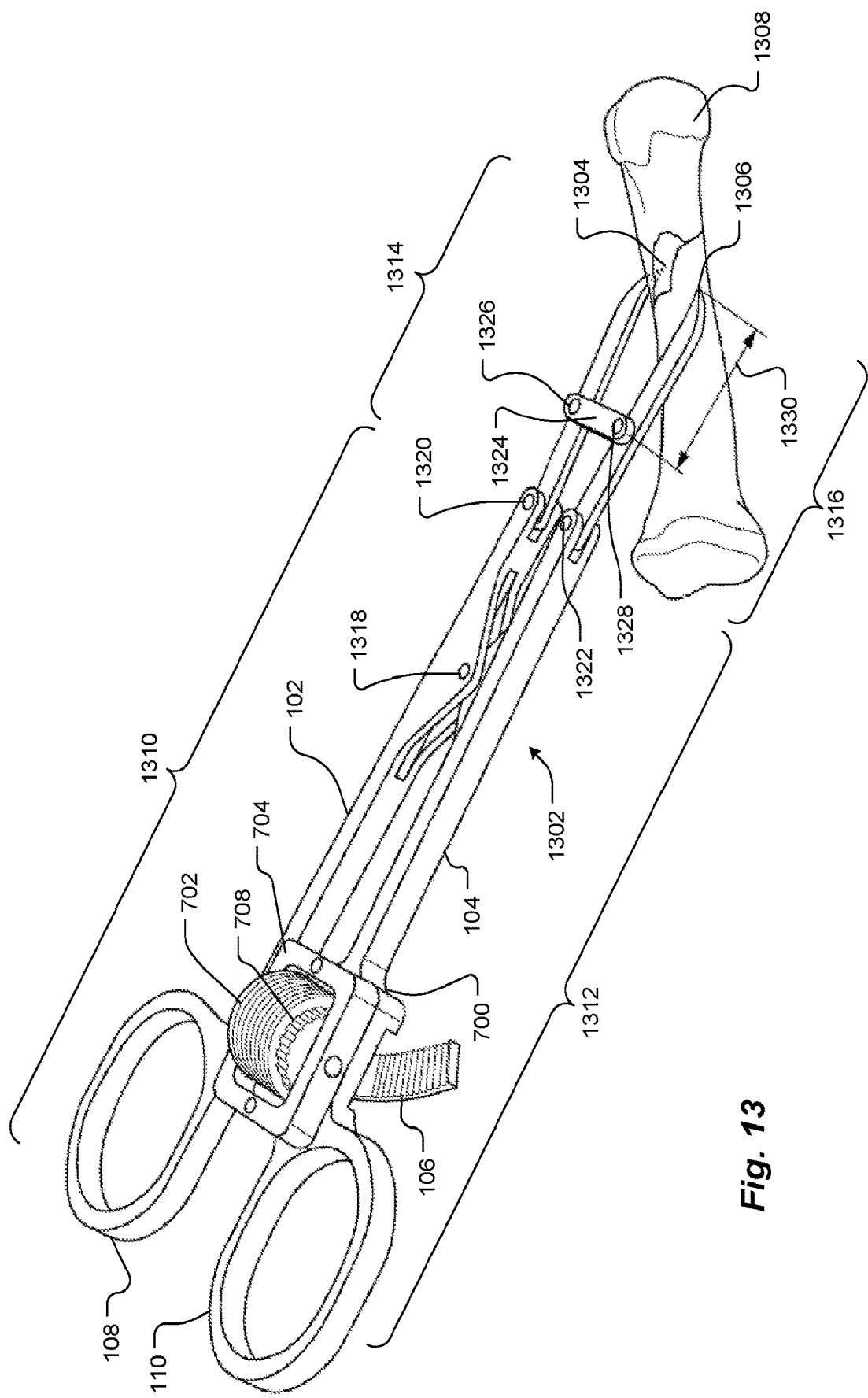
FIG. 13 is a perspective view of bone reduction forceps that include a five-bar linkage, according to an embodiment of the present invention.
Figures 14, 15:
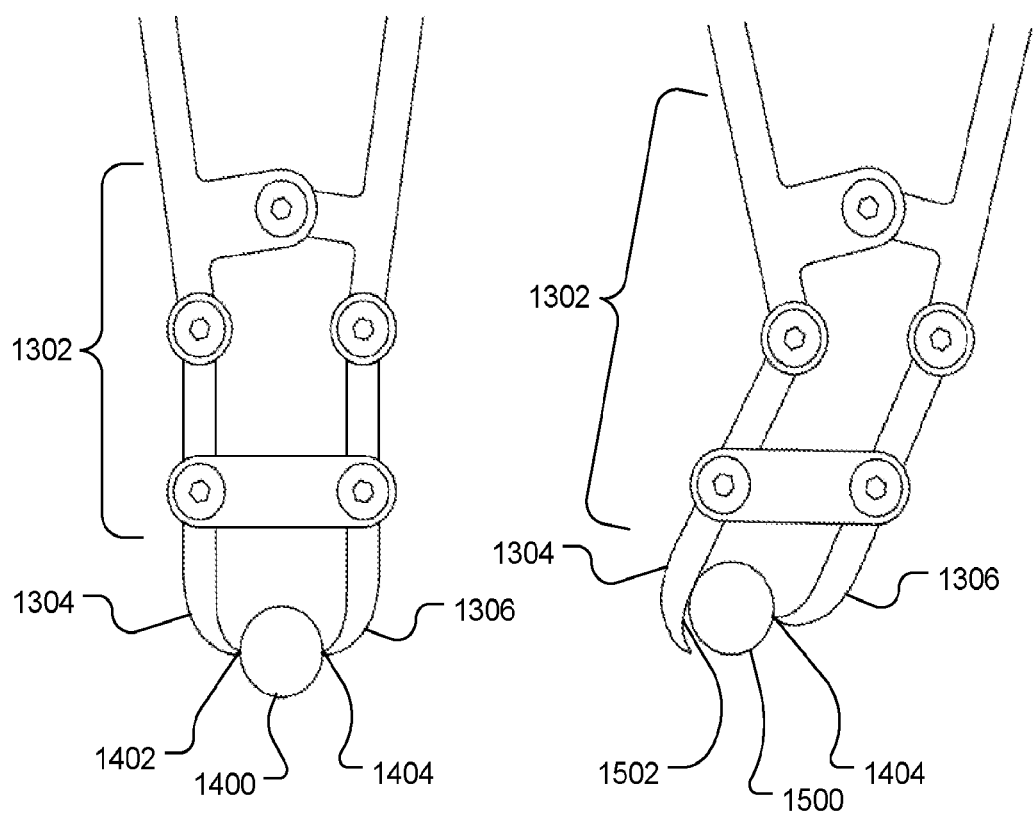
FIG. 14 is a top close-up view of tips of the five-bar linkage bone reduction forceps of FIG. 13, the tips grasping a bone in a first mode (between points of counterfacing tips), according to an embodiment of the present invention.
FIG. 15 is a top close-up view of the tips of the five-bar linkage bone reduction forceps of FIG. 13, the tips grasping a bone in a second mode (between a point of one tip and a curved face of a jaw of the other tip), according to an embodiment of the present invention.

While conventional bone reduction tools are based on a scissor-like, simple lever mechanism [6], [7], [8], [9], some forceps according to the present disclosure, exemplified by forceps 1300 schematically illustrated in FIG. 13, include a five-bar linkage 1302. This design gives a surgeon greater mechanical advantage and an additional degree of freedom at the tips 1304 and 1306, allowing for a more stable fracture alignment. The forceps 1300 with the five-bar linkage 1302 may operate in at least two modes, and the surgeon can grip bone 1308 in at least two ways: in a first mode, the tips 1304 and 1606 can capture bone 1400 between two sharp prongs 1402 and 1404, as illustrated in FIG. 14 or, in a second mode, the tips 1304 and 1606 can stabilize a bone fragment 1500 using the sharp point 1404 of one tip 1306 and a curved face 1502 defined by the other tip 1304, as illustrated in FIG. 15.

Returning to FIG. 13, the bone reduction forceps 1300 may include a five-bar linkage 1302 formed where, in conventional forceps 100 (FIG. 1), the ends of the first and second arms 102 and 104 would normally be the sites of tips 112 and 114 that engage bone. Instead, as shown in FIG. 13, each arm 102 and 104 contains a respective pivot joint 1320 and 1322, to which links are attached. Each of these links has another pivot joint 1326 and 1328, respectively, along its length. A connecting link 1324 joins the two pivot joints 1326 and 1328. Thus, the connecting link 1324 can be considered to connect two second arms to each other. At the ends of the second arms are tips 1304 and 1306 for engaging a bone 1308, or attachment points for attaching replaceable tips, as described herein.

Each of the first and second arms 102 and 104 includes a first portion 1310 and 1312, respectively, and a second portion, 1314 and 1316, respectively. The first portion 1310, 1312 includes the handle 108, 110 of the respective arm 102, 104 and a portion of a first joint 1318. The second portion 1314, 1316 includes the bone-engaging tip 1304, 1306 of the respective arm 102, 104. An end of the first portion 1310, 1312, opposite the handle 108, 110, is pivotally attached to an end of the second portion 1314, 1316, opposite the bone-engaging tip 1304, 1306, by a respective second joint 1320, 1322. The bone reduction forceps 1300 also include a connecting link 1324. One end of the connecting link 1324 is pivotally attached to the second portion 1314 of the first arm 102, between the bone-engaging tip 1304 and the end opposite the bone-engaging tip 1304, by a third joint 1326. Another end of the connecting link 1324 is pivotally attached to the second portion 1316 of the second arm 104, between the bone-engaging tip 1306 and the end opposite the bone-engaging tip 1306, by a fourth joint 1328. The first and second portions 1310, 1314 of the first arm 102, the first and second portions 1312, 1316 of the second arm 104, the connecting link 1326 and the first, second, third and fourth joints 1318, 1320, 1322, 1326 and 1328 collectively form the five-bar linkage 1302.

The five-bar linkage 1302 provides several advantages. In addition to the additional degree of freedom, the five-bar linkage 1302 provides a relatively large mechanical advantage, in a relatively small package. This reduces forces experienced by the worm gear 702 and rack 106, and thus reduces the possibility of material fatigue and failure, as well as making the device easier for a surgeon to operate. Furthermore, this design has the unique property of being under-constrained until gripping bone, at which point the additional contact with the bone fully constrains the system and makes the tips 1304 and 1306 stable.

To accommodate a human hand bone, the five-bar linkage 1302 should have a minimum dynamic range of about 4 mm closed to about 16 mm open. Additionally, the length 1330, from the tip 1304 of the device to the connecting link 1324 that joins the two jaws, should be greater than about 20 mm.

From these parameters, and also considering device aesthetics, placement of the center of mass and ergonomic considerations, nominal geometry of the device may be determined. To simplify the design process, the mechanical advantage may be estimated using the torque balance equation (Equation 2), in which A, B, C and D are respective distances between pairs of the joints 1318, 1320, 1322, 1326 and 1328 of the five-bar linkage 1302

$$\text{Force}_{tip} = \text{Force}_{applied} * \frac{A*C}{B*D} \quad (2)$$

Figure 16:
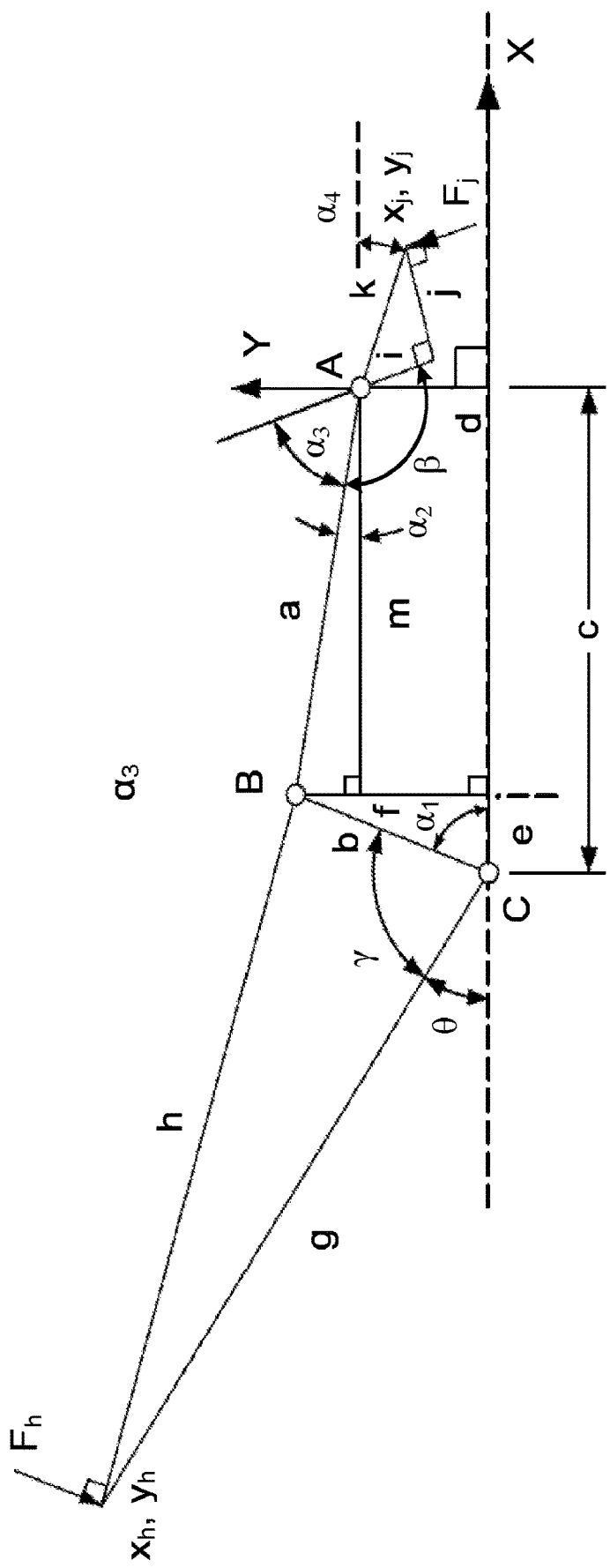
FIG. 16 is a schematic layout of the five-bar linkage of FIG. 13, according to an embodiment of the present invention.

The actual mechanical advantage (Table 2) may be calculated using a layout of the five-bar linkage in FIG. 16 and Equation Set 3.

$$\gamma = \cos^{-1}\left(\frac{b^2 + g^2 - h^2}{2bg}\right) \quad a_1 = \pi - \theta - \gamma \quad e = b\cos\alpha_1 \quad (3)$$

$$f = b\sin\alpha_1 \quad \alpha_2 = \sin^{-1}\left(\frac{f-d}{a}\right) \quad m = a\cos\alpha_2$$

$$c = m + e \quad k = \sqrt{i^2 + j^2} \quad \alpha_3 = \sin^{-1}\left(\frac{j}{k}\right)$$

$$\alpha_4 = \pi - \beta + \alpha_2 - \alpha_3 \quad x_h = -c - g\cos\theta \quad y_h = g\sin\theta$$

$$x_j = k\cos\alpha_4 \quad y_j = d - k\sin\alpha_4 \quad F_j = \frac{F_h\sqrt{dx_h^2 + dy_h^2}}{\sqrt{dx_j^2 + dy_j^2}}$$

TABLE 2

Five-Bar Linkage Typical Specifications

| | |
|---|---|
| Length | 155 mm |
| Mass | 0.09 kg |
| Grip range | 47 mm |
| Tip range | 4-16 mm |
| Mechanical advantage | 3.1-3.4 (angle dependent) |

A simple mathematical model of the linkages, such as a MATLAB script, may be used to select or optimize design parameters for a given embodiment.

To ensure that the device would not fail under maximum expected load, a Von Mises stress analysis of a prototype embodiment was done to a first order approximation and confirmed via finite-element analysis (FEA) in a SolidWorks simulation environment. The Von Mises stress equation is shown in Equation 4.

$$0.5[(\sigma_x-\sigma_y)^2+(\sigma_x-\sigma_z)^2+(\sigma_y-\sigma_z)^2+6(\tau_{xy}+\tau_{yz}+\tau_{xz})] \quad (4)$$

This analysis was performed for each of the beam members, treating the two handles 102 and 104 as the same in the first order approximation. The calculated and simulated values are listed in Table 3. All of the stresses are below the yield strength (760 MPa) of 17-4 PH stainless steel.

TABLE 3

Stress Values for Beam Members

| Member | Calculated maximum stress | Simulated maximum stress |
|---|---|---|
| Worm handle | 500 MPa | 710 MPa |
| Rack handle | 500 MPa | 680 MPa |
| Tip | 180 MPa | 180 MPa |
| Tip joint beam | 30 MPa | 20 MPa |

Pin Joints

Figure 17:
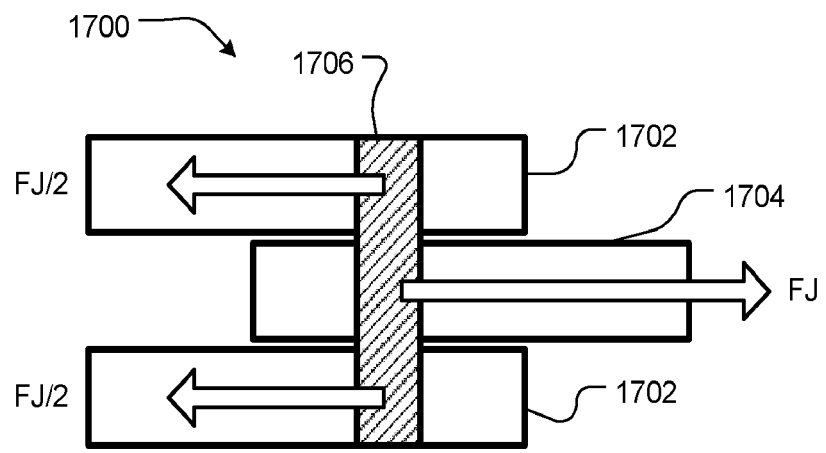
FIG. 17 is a schematic illustration of forces on a joint pin of the five-bar linkage of FIG. 13, according to an embodiment of the present invention.
Figure 18:
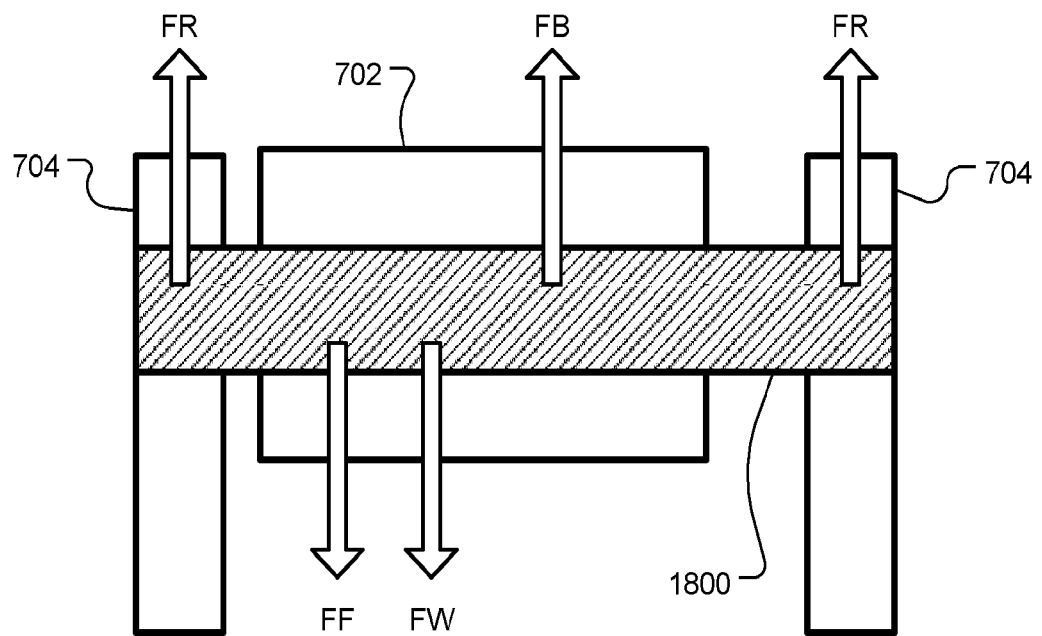
FIG. 18 is a schematic illustration of forces on a pin, on which is mounted the worm gear of the five-bar linkage of FIG. 13, according to an embodiment of the present invention.

All joints 1318-1322 and 1326-1328 in the forceps 1300 may be clearance (fixed side) and press-fit (moving side) pin joints, although other suitable types of joints (e.g., with a bearing sleeve or even molded living hinge) may be used. In some embodiments, five M2 cylindrical solid pins, each 4.76 mm long, are used in the five-bar linkage 1302, as schematically illustrated in FIG. 17. In FIG. 17, a pinned joint 1700 is formed between two members 1702 and 1704 by a pin 1706. As shown schematically in FIG. 18, one cylindrical solid pin 1800, 22.23 mm long, is used to support the worm gear 702 within the rectangular frame 704.

In FIG. 17, FJ indicates force at the joint, FR indicates reaction force from the support, FB indicates normal force from the rack (5 N), FF indicates force from a user's finger to engage the worm (10 N), and FW indicates weight of the pin and worm (about 0.025 N). To ensure the pins would not fail under the maximum expected load, the pins were analyzed as simply supported beams in bending for their maximum tensile, compressive and shear stresses using Equations 5 and 6.

$$\sigma = M_{max} * c / I \quad (5)$$

$$I = \frac{\pi}{4} * \left(\frac{D}{2}\right)^4 \quad (6)$$

Figure 19:
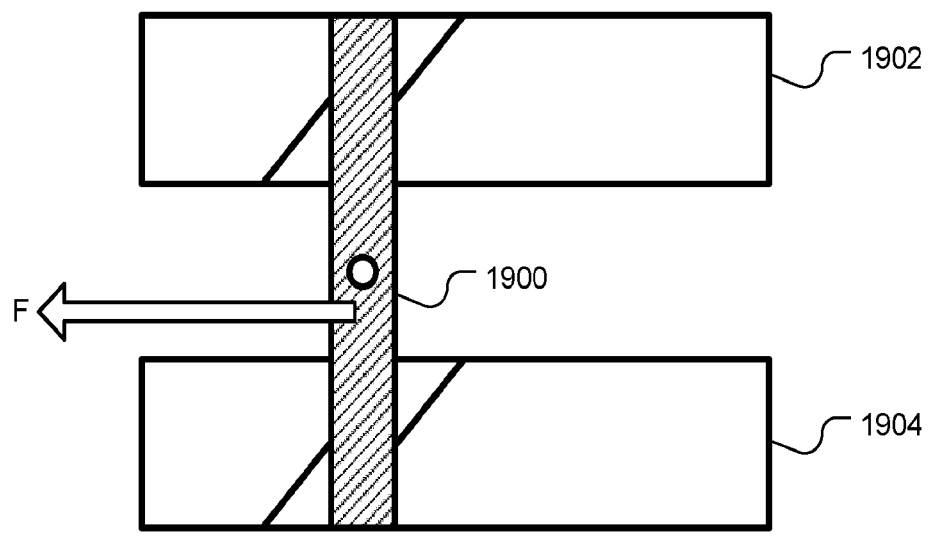
FIG. 19 is a schematic illustration of off-center forces on a joint pin of the five-bar linkage of FIG. 13, according to an embodiment of the present invention.

The contact stresses due to off-center forces on the pins were also calculated using FIG. 19 (in which a pin 1900 joins two members 1902 and 1904) and Equation 7, where F is the off-center force, t is thickness of the members, M is moment applied by the off-center force and $A_{contact}$ is contact area of the pin 1900 on the member 1902 or 1904. The Von Mises stress and safety factors were calculated for the pins. All of the pins had safety factors significantly above 1, as summarized in Table 4.

$$\sigma = M \bigg/ \left(4 * A_{contact} * 0.5 * \left[\frac{2}{3} * \frac{t}{2}\right]\right) \quad (7)$$

TABLE 4

Von Mises Stresses and Safety Factors for Pins

| Pin Location | Von Mises Stress | Safety Factor |
|---|---|---|
| Joint A | 387 MPa | 2.7 |
| Joint B | 193 MPa | 5.3 |
| Joint C | 257 MPa | 4.0 |
| Worm gear | 2.43 MPa | 425 |

Figure 20:
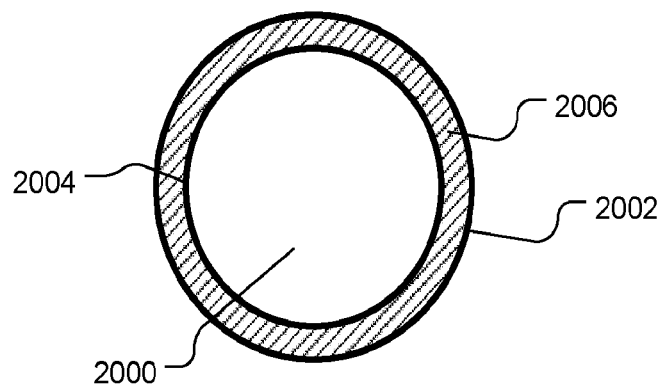
FIGS. 20-22 are schematic cross-sectional views illustrating respective ideal, worst case loose and worst case tight interference fits of pins, according to embodiments of the present invention.
Figure 21:
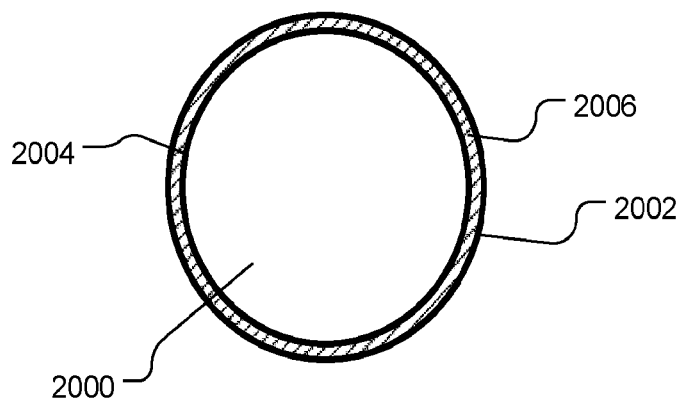
Figure 22:
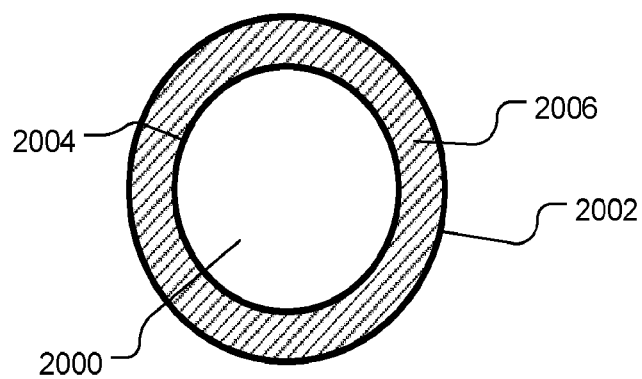

The pins were also analyzed for failure during the press fit process using standard machine design engineering equations, such as equations available at [10]. FIG. 20 schematically illustrates an ideal interference fit, in which an inner body (IB) 2000 is pressed into a void defined by an outer body (OB). The inner body outside diameter (IBOD) is indicated at 2002. The outer body inside diameter (OBID) is indicated at 2004. The IBOD is greater than the OBID 2004, i.e., an interference fit, and the diametrical interference is equal to (OBID−IBOD), indicated by hashed lines at 2006. A worst case for a loose interference fit, in which case the joint may not be able to transmit a desired force or torque, is schematically illustrated in FIG. 21. A worst case for a tight interference fit, in which case yield stresses may be exceeded and the outer body may rupture, is schematically illustrated in FIG. 22.

The pinned joints may be assembled with an interference of about 0.01 mm and a tolerance of about 0.01 mm. To achieve a safety factor of 1 or greater, the pins and members should be press fit at higher-than-room temperature, allowed to yield, and then cooled.

Fabrication

The nominal shape of most links may be cut using a waterjet machine or other suitable process, such as fine blanking or forging for high volume production. The pin joints may be simple tang and clevis joints, which can be made using relatively simple operations on a milling machine, or other suitable joints. Desirable for its high strength and corrosion resistance properties, 17-4 PH stainless steel in full- or half-hard state is preferred, although conventional surgical grade stainless steel or titanium may also be used. For light forces, high strength molded plastic forceps could also be created for one-time use. The worm gear can be made of brass, and the pins can be made from high strength surgical grade stainless steel, as is known in the art of surgical forceps and clamp design.

The support piece 704 for the worm gear 702 may be machined as a monolithic piece with the forceps handle below, instead of a separate attached component, to reduce the number of components and decrease size. The brass worm gear 702 may be knurled, or a thumb wheel may be attached to facilitate turning the worm gear 702 with gloved fingers.

Other products containing different combinations of the three modules (five-bar linkage, rack and worm and/or interchangeable tips) are anticipated, such as to accommodate surgeon preference. In particular, forceps with standard tips, the simple (first class) lever mechanism and the rack 106 and worm gear 702 may be machined from 17-4 PH or surgical grade stainless steel. Titanium may also be used for the components, including the pins. Such an embodiment offers the benefit of continuous force adjustment to surgeons that prefer a simple lever mechanism.

Interchangeable/Replaceable Tips

Figure 23:
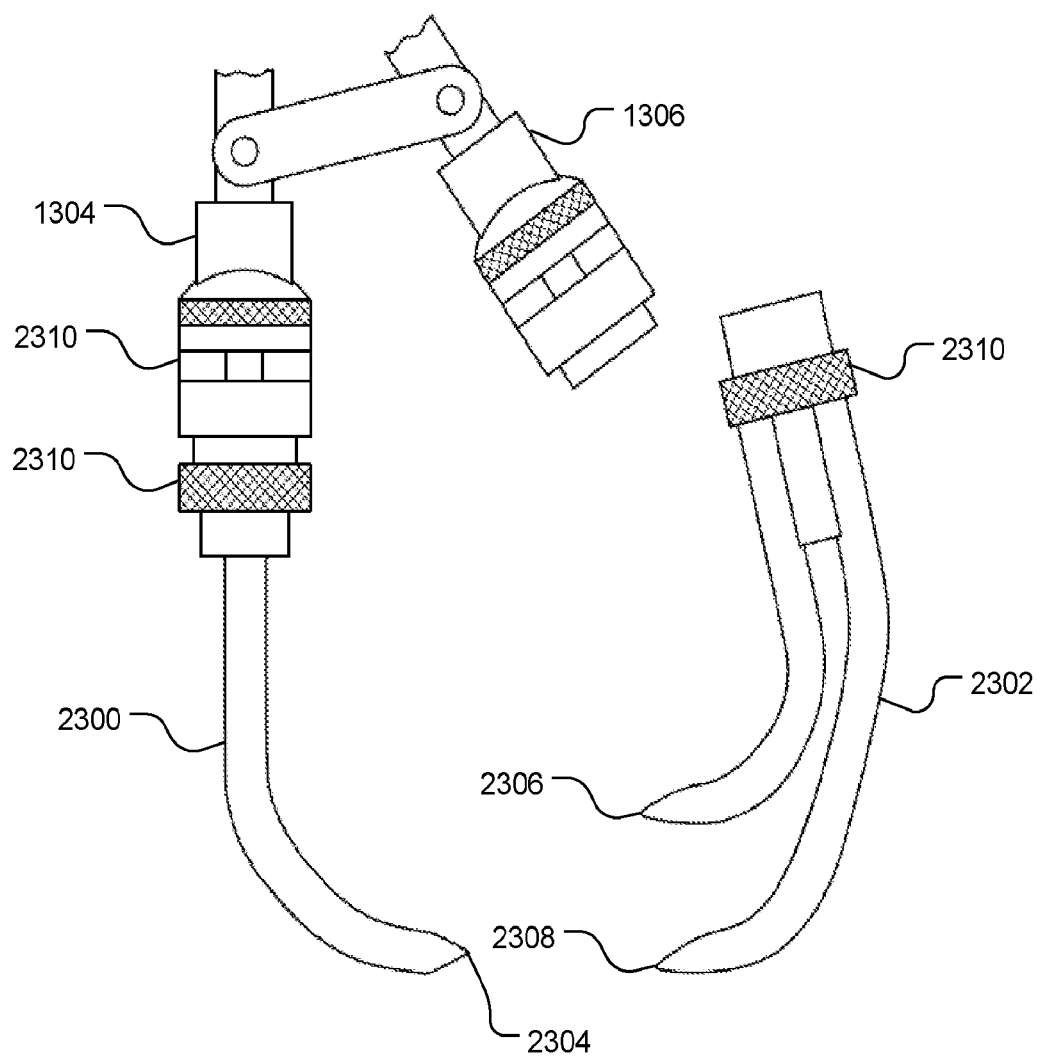
FIG. 23 is a schematic top view of interchangeable tips for bone reduction forceps, according to an embodiment of the present invention.

As noted, using forceps with conventional tips, a surgeon is unable to fully constrain a bone. Even at maximum tightness, the forceps are free to rotate around the axis connecting the tips. While some forceps use three-point tips to provide additional constraint, this clutters the surgical site and cannot always be used in small surgical spaces. To overcome this problem, some embodiments include detachable tips, as exemplified in FIG. 23 by tips 2300 and 2302, which allow a surgeon to choose an optimal tip geometry for each particular surgery. Each of these detachable tips, 2300, 2302 may include one, two or more prongs, as exemplified by prongs 2304, 2306 and 2308, and is connected to the forceps via a standard Luer lock 2310, a press fit junction (not shown), a self-locking taper junction, (not shown), a threaded connector (not shown) or other suitable reattachable junction. A single tool, with an entire set of interchangeable tips 2300-2302, drastically reducing the cost and variety of tools necessary in a surgical suite, while providing the surgeon with the best possible options.

The ease of exchanging tips was evaluated by timing the overall process. The Luer lock method was both easy to use and intuitive, requiring fewer than 10 seconds to swap tips.

Testing

To quantitatively evaluate efficacy of the forceps 1300 (FIG. 13), the continuous force control aspect was analyzed and compared to standard bone reduction forceps 100 (FIG. 1) with a ratcheting mechanism. A simple circuit using a force sensitive resistor (FSR) in series with a 100 kOhm resistor formed a voltage divider. An analog output from the voltage divider was recorded via a PSoC 4 microcontroller and processed in MATLAB. The FSR was placed between two 3D printed pieces to provide even force distribution across the FSR when clamped. Metal pads were added to the outside of the 3D printed parts to further ensure even force distribution and to mediate the effects of data drift due to the sharp tips digging into the soft plastic. This test setup was then characterized by taking ten readings with known amounts of force applied and performing a least squares regression curve fit in MATLAB. Finally the standard bone reduction forceps 100 and the forceps 1300 were analyzed by clamping onto the FSR, and the resulting forces were recorded.

Figure 24:
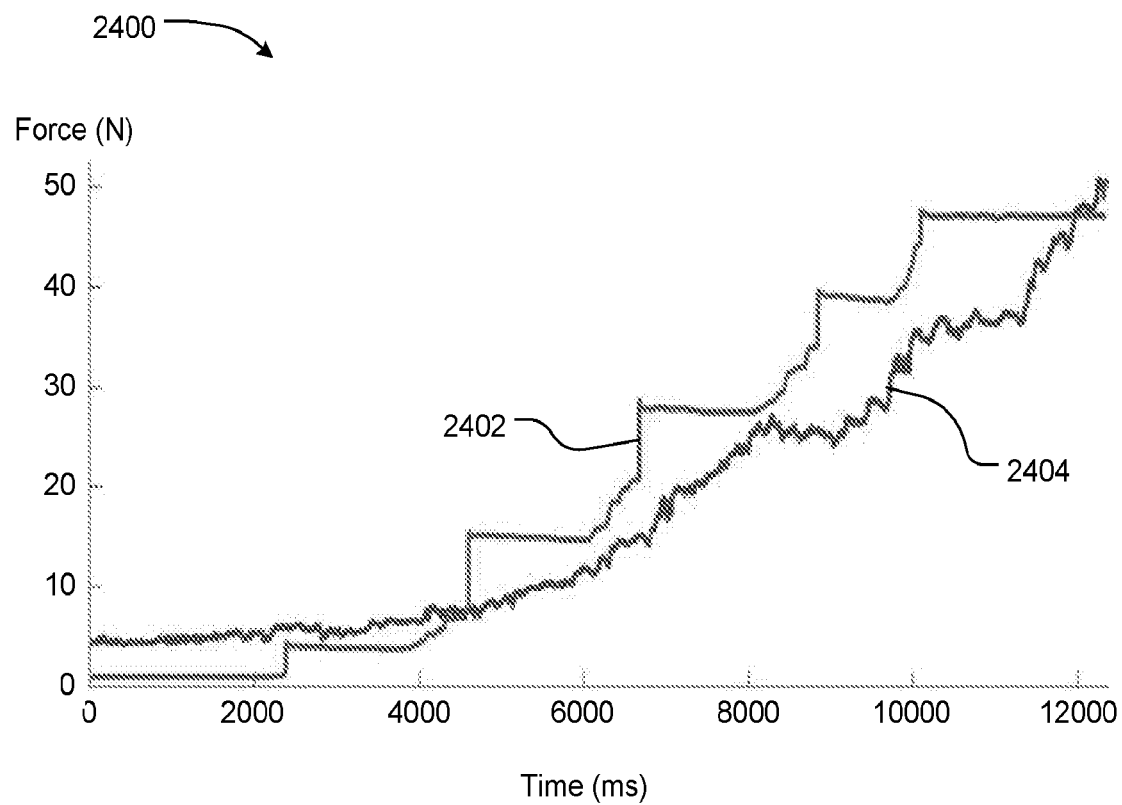
FIG. 24 is a graph of clamping forces exerted by the prior art bone reduction forceps of FIG. 1 and the bone reduction forceps that include the worm gear drive of FIG. 7.

A quantitative gripping force comparison graph 2400 can be seen in FIG. 24, in which plot line 2402 represents force exerted by the conventional forceps 100, and plot line 2404 represents force exerted by the forceps 1300. The standard bone reduction forceps 100 are capable of achieving only discrete force applications, thus the step-like form of the data 2402. The flat lines indicate stable force applications, which are approximately 10-15N apart. Comparatively, the forceps 1300 was able to achieve relatively infinitely adjustable force 2404 application. The oscillatory behavior of the forceps 1300 is likely partially due to user error in turning the worm gear. However, in testing it was noticed that with both devices, using the described test setup, if the force application was changed in any way, either by ratcheting or the worm gear, there was a small overshoot before the force stabilized. This could be due to the plastic supporting the FSR deforming, or it could be the devices settling into minimal energy states.

Qualitative tests were conducted using chicken bones of similar diameter to human hand bones. These bones were fractured by hand and held under compression with surgical tubing to mimic forces applied to fractured bone by tendons and ligaments, similar to the arrangement shown in FIG. 13. Performance of the forceps 1300 was compared to the conventional bone reduction forceps 100 (FIG. 1).

A hand surgeon tester deemed the prototyped forceps 1300 to be equally comfortable as the conventional forceps 100. Furthermore, he found the worm gear simple to operate, allowing him to easily make both gross and fine adjustments in the clamping force. The tester also noted that it took less force to clamp on to the bone, which is likely due to both the increased mechanical advantage provided by the five-bar linkage 1302, and the smaller step size of the prototype's rack 106 compared to the conventional forceps 100.

The prototype forceps 1300 were able to clamp both oblique and transverse fractures. Transverse fractures are traditionally difficult to clamp with standard forceps, often requiring two separate forceps to bring the bones into alignment. However, the worm gear and rack system of the prototype was able to apply the correct amount of force to stabilize the fracture, without pushing the bones out of alignment.

To test the stability of clamping with the prototyped forceps 1300, the rig was rotated, as a hand would be during intraoperative X-ray imaging. The clamped bones were also hit, simulating the hand knocking a table during the imaging, a common surgical occurrence. The prototyped forceps remained clamped to the fractured bones during the entire test and anatomic alignment was not compromised.

The five-bar linkage 1302 of the prototyped forceps 1300 provided an additional method for the tester to clamp the bone fracture. The tester was able to clamp an oblique fracture by clamping with either the two ends of the tips 1304 and 1306, or the end of one tip and the curved face of the other (see FIG. 15). The tester considers this to be a real advantage of the prototyped forceps 1300, making it easier to clamp the bone.

The disclosed bone reduction forceps were found to more effectively and more easily reduce fractured bone than standard forceps. Qualitative end-user testing by the tester found the prototype forceps to be similar in comfort and ease of use as the current forceps, but more effective in achieving desired clamping force. Furthermore, the five-bar linkage provided the tester an equally effective second method of clamping the bone. Quantitative testing indicated that the disclosed forceps allowed continuous adjustment of clamping force, while current forceps could only increase clamping force in discrete 10 Newton intervals, and only completely release. The disclosed forceps enabled the tester to continuously adjust the clamping force and obtain a desired clamping force. As a result, the disclosed forceps are expected to improve user satisfaction, decrease surgical time and allow easier and faster achievement of anatomic alignment in fracture reduction.

Alternative Design

Figure 25:
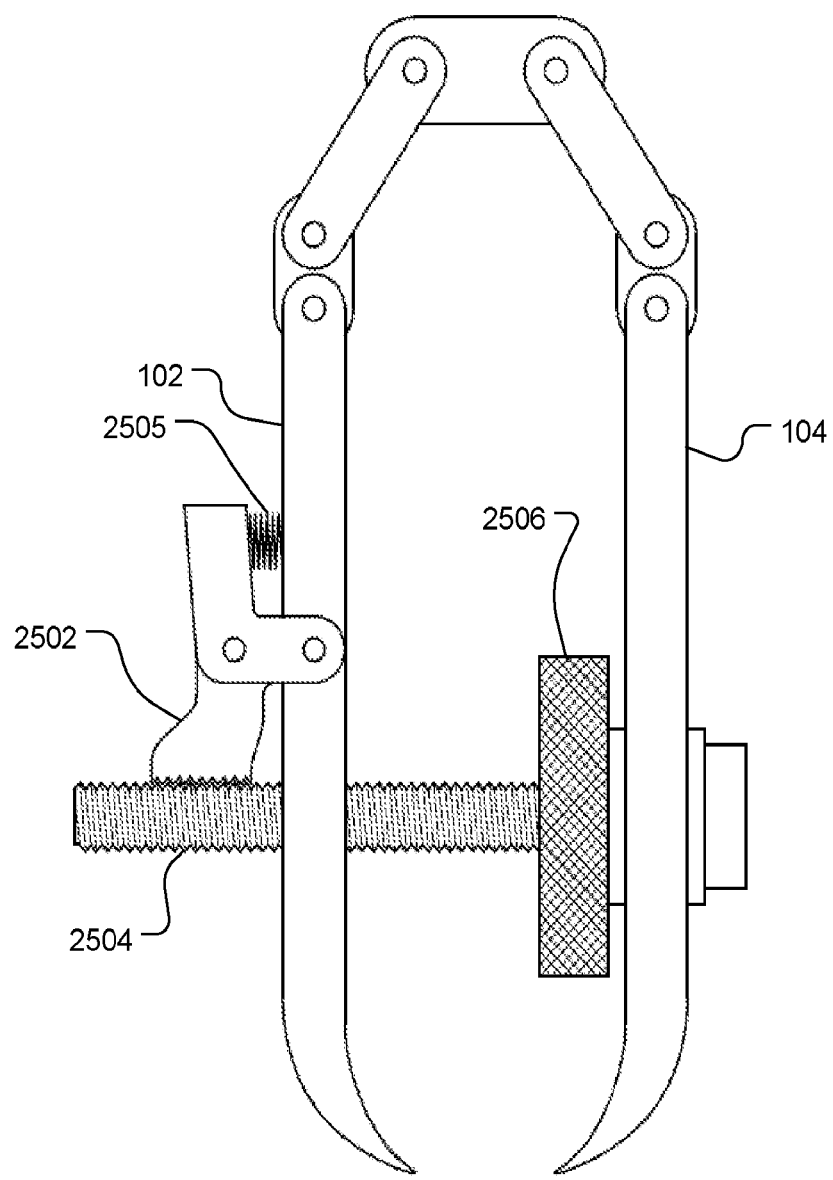
FIG. 25 is a schematic top view of bone reduction forceps, according to an alternative embodiment of the present invention.

Alternatively designed forceps 2500 are shown schematically in FIG. 25. Instead of the worm gear and rack mechanism, the forceps 2500 incorporate a dial nut ("half nut") 2502 and screw 2504. The dial nut or 2502 may be preloaded against the screw 2504 by a spring 2505, such that, similar to the worm gear and rack design, the forceps 2500 may be closed in a unidirectional manner discretely and then fine adjustment could be achieved bi-directionally by turning the screw. A thumb wheel 2506 may be included to facilitate turning the screw 2504. This design was also prototyped and tested.

All concepts disclosed herein can be generalized to bone reduction forceps for larger bones, and other surgical tools that require, or would benefit from, fine control of clamping force.

Unless otherwise indicated in context, or would be understood by one of ordinary skill in the art, terms such as "about" mean within ±20%. As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

REFERENCES

[1] Karl, J W, et al., The Epidemiology of Upper Extremity Fractures in the United States, 2009, Journal of Orthopedic Trauma 29.8 (2015): 242-244, Pubmed, Online.
[2] Fricker, R., et al., Metacarpals—Long oblique (spiral) fracture, The AO Foundation, 8 Sep. 2008, Web. 12 Dec. 2015.
[3]: Fricker, R., et al., Metacarpal Fractures, The AO Foundation, 8 Sep. 2008, Web. 12 Dec. 2015.
[4] Bernstein M L, Chung K C, 2006, Hand fractures and their management: an international view, Injury 37 (11), 1043-1048.
[5] Connor, J., 2015, Hand Surgeon at Mount Auburn Hospital, USA, private communication.
[6] Orthomed, Inc., Orthomed Bone Holding Instruments, Web. 12 Dec. 2015.
[7] Stryker Leibinger Instruments for Hand Surgery, Stryker, 2005, Web. 13 Dec. 2015.
[8] Bone Clamp Forceps, Millennium Surgical, Web. 13 Dec. 2015.
[9] Gautier, Emanuel and Rodrigo F Pesantez, Reduction Techniques—Reduction forceps, Ruedi, T. P., et al., AO Principles of Fracture Management, The AO Foundation Publishing, Web. 12 Dec. 2015.
[10] Slocum, A. H., Precision Machine Design, 1995, Society of Manufacturing Engineers, Dearborn, Mich.

What is claimed is:

1. Bone reduction forceps, comprising:
a first arm having a handle proximate one end and a first bone-engaging tip proximate an opposite end of the first arm;
a second arm having a handle proximate one end and a second bone-engaging tip proximate an opposite end of the second arm, the second arm being pivotally attached to the first arm by a first joint disposed between the respective handles and the respective first and second bone-engaging tips of the first and second arms;
a rack attached to the first arm between the first joint and the handle of the first arm; and
a worm gear rotatably attached to the second arm between the first joint and the handle of the second arm, the worm gear being oriented and configured to disengageably engage the rack and provide, in a first operating mode, continuous forceps closure force adjustment in response to rotation of the worm gear and, in a second operating mode in which the rack and the worm gear act as a ratchet, discrete forceps closure force adjustment.

2. Bone reduction forceps according to claim 1, wherein:
the rack comprises a curved planar rack attached to the first arm, between the first joint and the handle of the first arm;
the rack extends along an arc toward the second arm and passes beneath the second arm; and
a center of radius of the rack is disposed proximate the first joint.

3. Bone reduction forceps according to claim 1, further comprising a thumbwheel attached for rotation with the worm gear.

4. Bone reduction forceps according to claim 1, further comprising a thumbwheel as an integral part of the worm gear for rotation with the worm gear.

5. Bone reduction forceps according to claim 1, wherein the rack and the worm gear each has a buttress thread profile.

6. Bone reduction forceps according to claim 1, wherein the rack comprises a plurality of teeth, each tooth having a respective slip side face and a respective lock side face, the slip side face forming an angle of about 25-65°, relative to a normal axis between the rack and the worm gear, and the lock side face forming an angle of about 0-20°, relative to the normal axis.

7. Bone reduction forceps according to claim 1, wherein the rack comprises a plurality of teeth, each tooth having a respective slip side face and a respective lock side face, the slip side face forming an angle of about 25-65°, relative to a normal axis between the rack and the worm gear, and the lock side face forming an angle of about 0-20°, relative to a line perpendicular to a rotation axis of the worm gear.

8. Bone reduction forceps according to claim 1, wherein the rack comprises a plurality of teeth having a pitch of about 1/18 inch (1.4 mm).

9. Bone reduction forceps according to claim 1, wherein at least one tip of the first bone-engaging tip and the second bone-engaging tip defines a curved surface that, in at least one mode, counterfaces the other tip.

10. Bone reduction forceps according to claim 1, wherein: each of the first and second arms comprises:
    a first portion that includes the handle of the respective arm and a portion of the first joint; and
    a second portion that includes the respective bone-engaging tip of the respective arm; and
    wherein an end of the first portion, opposite the handle, is pivotally attached to an end of the second portion, opposite the respective bone-engaging tip, by a respective second joint; the bone reduction forceps further comprising:
a connecting link, one end of the connecting link being pivotally attached to the second portion of the first arm, between the bone-engaging tip and the end opposite the bone-engaging tip, by a third joint, and another end of the connecting link being pivotally attached to the second portion of the second arm, between the bone-engaging tip and the end opposite the bone-engaging tip, by a fourth joint, wherein the first and second portions of the first arm, the first and second portions of the second arm, the connecting link and the first, second, third and fourth joints collectively forming a five-bar linkage.

11. Bone reduction forceps according to claim 1, wherein:
    the first bone-engaging tip is reattachably attached to the first arm; and
    the second bone-engaging tip is reattachably attached to the second arm.

12. Bone reduction forceps according to claim 11, wherein each bone-engaging tip is reattachably attached to the respective arm by a respective threaded connector.

13. Bone reduction forceps according to claim 11, wherein each bone-engaging tip is reattachably attached to the respective arm by a respective Luer lock connector.

14. Bone reduction forceps according to claim 11, wherein each bone-engaging tip is reattachably attached to the respective arm by a respective press fit connector.

15. Bone reduction forceps according to claim 11, wherein each bone-engaging tip is reattachably attached to the respective arm by a respective self-locking taper fit connector.

16. Bone reduction forceps according to claim 11, wherein:
    the bone-engaging tip of the first arm comprises a one-prong tip; and
    the bone-engaging tip of the second arm comprises a one-prong tip; the bone reduction forceps further comprising:
    a third bone-engaging tip comprising a two-prong tip, the third bone-engaging tip being reattachably attachable to the first arm in place of the one-prong bone-engaging tip of the first arm.

17. Bone reduction forceps according to claim 11, wherein:
    each of the first and second arms comprises:
        a first portion that includes the handle of the respective arm and a portion of the first joint; and
        a second portion that includes the respective bone-engaging tip of the respective arm; and
        wherein an end of the first portion, opposite the handle, is pivotally attached to an end of the second portion, opposite the respective bone-engaging tip, by a respective second joint; the bone reduction forceps further comprising:
    a connecting link, one end of the connecting link being pivotally attached to the second portion of the first arm, between the bone-engaging tip of the first arm and the end opposite the bone-engaging tip of the first arm, by a third joint, and another end of the connecting link being pivotally attached to the second portion of the second arm, between the bone-engaging tip of the second arm and the end opposite the bone-engaging tip of the second arm, by a fourth joint, wherein the first and second portions of the first arm, the first and second portions of the second arm, the connecting link and the first, second, third and fourth joints collectively forming a five-bar linkage.

18. Bone reduction forceps, comprising:
a first arm having a handle proximate one end and a first bone-engaging tip proximate an opposite end of the first arm;
a second arm having a handle proximate one end and a second bone-engaging tip proximate an opposite end of the second arm, the second arm being pivotally attached to the first arm by a first joint disposed between the respective handles and the respective first and second bone-engaging tips of the first and second arms;
a rack attached to the first arm between the first joint and the handle of the first arm;
wherein each of the first and second arms comprises:
    a first portion that includes the handle of the respective arm and a portion of the first joint; and
    a second portion that includes the respective bone-engaging tip of the respective arm; and
    wherein an end of the first portion, opposite the handle, is pivotally attached to an end of the second portion, opposite the respective bone-engaging tip, by a respective second joint; the bone reduction forceps further comprising:
a connecting link, one end of the connecting link being pivotally attached to the second portion of the first arm, between the bone-engaging tip of the first arm and the end opposite the bone-engaging tip of the first arm, by a third joint, and another end of the connecting link being pivotally attached to the second portion of the second arm, between the bone-engaging tip of the second arm and the end opposite the bone-engaging tip of the second arm, by a fourth joint, wherein the first and second portions of the first arm, the first and second portions of the second arm, the connecting link and the first, second, third and fourth joints collectively forming a five-bar linkage.

19. Bone reduction forceps according to claim 18, wherein
    the first bone-engaging tip is reattachably attached to the first arm; and
    the second bone-engaging tip is reattachably attached to the second arm.

20. Bone reduction forceps according to claim 19, wherein each bone-engaging tip is reattachably attached to the respective arm by a respective threaded connector.

21. Bone reduction forceps according to claim 19, wherein each bone-engaging tip is reattachably attached to the respective arm by a respective Luer lock connector.

22. Bone reduction forceps according to claim 19, wherein each bone-engaging tip is reattachably attached to the respective arm by a respective press fit connector.

23. Bone reduction forceps according to claim 19, wherein each bone-engaging tip is reattachably attached to the respective arm by a respective self-locking taper fit connector.

\* \* \* \* \*